United States Patent [19]

Hartman

[11] Patent Number: 5,018,531
[45] Date of Patent: May 28, 1991

[54] SKIN BLEMISH MEASURING AND RECORDING SYSTEM AND METHOD

[76] Inventor: William B. Hartman, 8 Sheffield Rd., North Caldwell, N.J. 07006

[21] Appl. No.: 403,962

[22] Filed: Sep. 7, 1989

[51] Int. Cl.⁵ .............................................. A61B 5/10
[52] U.S. Cl. ................................... 128/774; 206/569; 33/483
[58] Field of Search .............. 128/771, 774, 775, 778; 33/483, 494; 206/569

[56] References Cited

U.S. PATENT DOCUMENTS

| | | | |
|---|---|---|---|
| 1,904,234 | 4/1933 | Hoskin et al. | 128/774 |
| 3,230,628 | 1/1966 | Hite | 33/483 |
| 4,097,997 | 7/1978 | Bjornson | 128/774 |
| 4,131,998 | 1/1979 | Spears | 128/774 |
| 4,569,358 | 2/1986 | Gormley | 128/774 |

Primary Examiner—Max Hindenburg
Attorney, Agent, or Firm—Blum Kaplan

[57] ABSTRACT

A system to record the color, size and location of skin blemishes on the skin using an objective standard is provided. The system includes a color scale containing colors and shades of colors sufficient to portray a skin blemish; a blemish-size gauge for measuring the size of the blemish; a distance scale for measuring the distance of the blemish from reference points; and a body map of the skin surface of the entire human body with reference points for recording the location of the blemish. Each color in the color scale and size in the size gauge is given an individual designation for easy reference. The color scale and the measuring devices may be combined in one multi-functional tool and with a folded chart for easy storage in a folder to protect the colors from changes due to exposure to light.

20 Claims, 5 Drawing Sheets

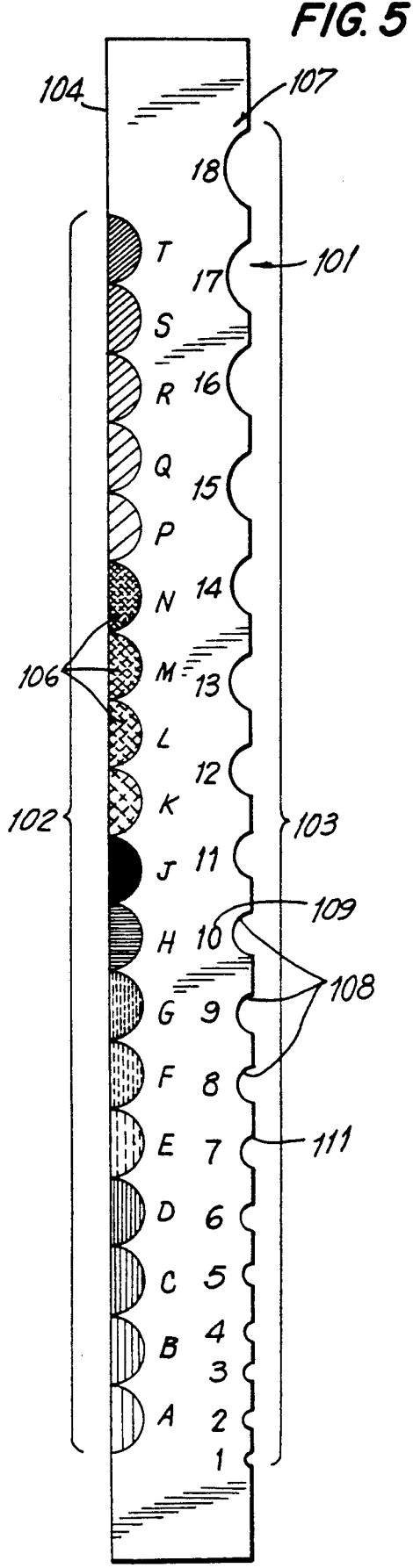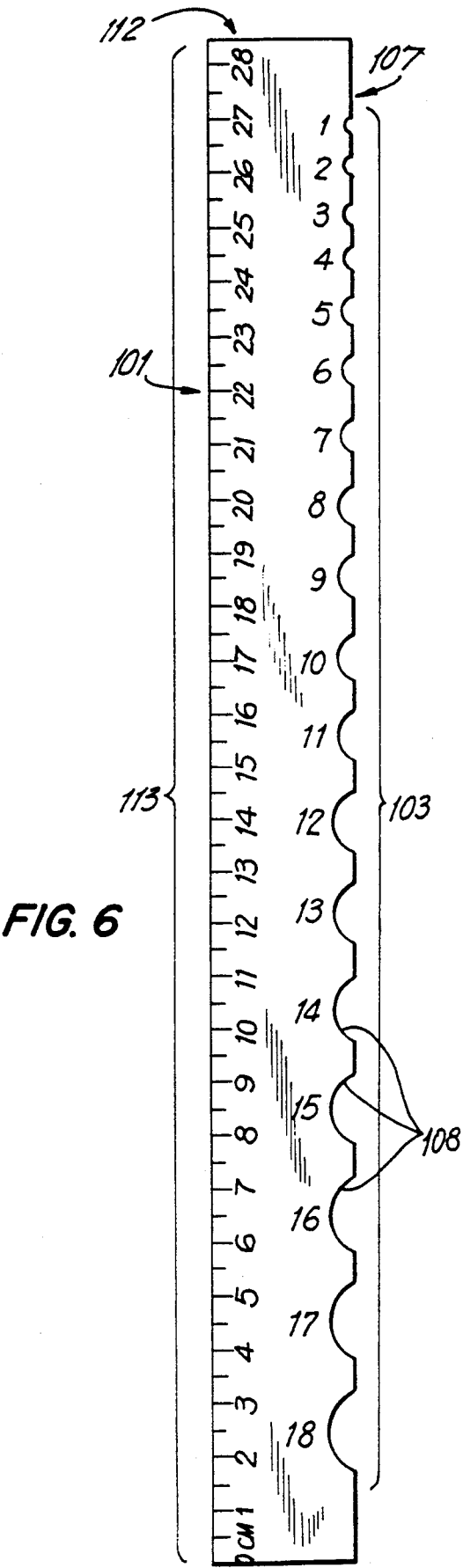

SKIN BLEMISH MEASURING AND RECORDING SYSTEM AND METHOD

BACKGROUND OF THE INVENTION

This invention relates generally to a skin blemish measuring and recording system, and more particularly to a system and method of quantifying, comparing, measuring and recording a characterization of skin blemishes, including a blemish-color reference scale, a blemish-size gauge and a distance scale and a map of the surface of the human body for recording the collected data.

As used in this application, "skin" refers to the membrane tissue forming the external covering of the human body, the subcutaneous tissue, the epidermis and dermis and other parts or layers referred to as skin. "Blemish" denotes a flaw, defect or disfigurement, not of normal appearance. For the purpose of this application, "blemish" includes a mole, discoloration, mark, abnormality or irregularity of the skin. "Skin blemish" is the combination of the above, namely such a flaw, defect or disfigurement located on the epidermis or dermis.

Skin diseases and abnormalities are increasingly common ailments. Currently, over a half million Americans each year develop some kind of skin cancer. Moreover, experts predict a fourfold increase in skin cancers by the end of the century due in large measure to increased leisure time which results in increased exposure to the sun, air pollutants and increased exposure to UV radiation due to ozone depletion. For successful treatment of the cancer and other diseases, however, early detection of abnormal skin growths or changes in the appearance of skin blemishes is crucial. Yet because some of those marks are small and grow slowly, it is almost impossible for a layman to know when or if to seek medical attention. Even for doctors, it can be difficult to recognize and record using descriptive language the precise characterization of the blemishes necessary to detect any changes over time and determine their rate of growth or color change. Even photographs, which are dependent on lighting conditions, may not accurately represent the color of the blemishes. Thus, a slight change in size and/or color of a blemish may be a significant and helpful observation and may lead to an opportunity for an early professional diagnosis of an infection, disease or cancer.

Accordingly, it is desirable to provide an improved system and method which establishes an objective standard for locating, measuring, distinguishing by color and recording skin blemishes.

SUMMARY OF THE INVENTION

Generally speaking, in accordance with the invention, a system and method for measuring objectively the appearance of any blemish as defined above and any other indicia on the skin and accurately recording the data objectively is provided. The system includes a blemish-color scale for determining color of the blemish, a blemish-size gauge for measuring the size of the blemish and a distance scale for measuring the location of the blemish from certain fixed body reference points. The collected data is recorded on a body map or chart.

The color scale includes between approximately 12 to 36 colors and shades of colors selected to identify the colors of a variety of skin blemishes. The blemish-size gauge used to measure the size of the blemish includes indicia sufficient to record sizes ranging from about one millimeter to twenty millimeters. The distance scale is approximately 30 centimeters long for measuring distance(s) from reference points. The map or chart of the body depicts the entire skin surface of the body with reference points to aid in accurate location.

Each color and size appearing on the color scale and size gauge is given individual letter or number designations for easy reference. The blemish-color scale, blemish-size gauge and the distance scale may be combined in one multi-functional tool. The body map may folded and stored with the multi-functional tool in a folder to protect the color scale from degradation due to exposure to light and for easy storage.

Accordingly, it is an object of the invention to provide a system and method for recording the color, size and location of a blemish on the skin to facilitate recognition of any subsequent change in color and size.

Another object of the invention is to provide an improved device for accurately identifying the color and measuring the size of a blemish on the skin.

A further object of the invention is to provide a unique color scale including a plurality of colors for identifying the color of skin blemishes.

Still another object of the invention is to provide a device for measuring the size of a blemish on the skin using a size gauge and/or a distance scale.

Still a further object of the invention is to provide a map of the human body with designated reference points to facilitate recording the location, color and size of the skin blemish.

Yet another object of the invention is to provide a method for measuring size, color and location of skin blemishes and recording each observation for future reference and comparison to aid in the early detection of changes in the size or color of the recorded blemishes.

Still other objects and advantages of the invention will in part be obvious and will in part be apparent from the specification.

The invention accordingly comprises the several steps and the relation of one or more of such steps with respect to each of the others, and the article possessing the features, properties and the relation of elements, which are exemplified in the following detailed disclosure, and the scope of the invention will be indicated in the claims.

BRIEF DESCRIPTION OF THE DRAWINGS

For a fuller understanding of the invention, reference is made to the following description taken in connection with the accompanying drawings, in which:

FIG. 5 is a top plan view of a multi-functional measuring device showing a blemish-color scale and blemish-size gauge;

FIG. 6 is a rear plan view of the multi-functional measuring device of FIG. 5 showing the distance scale and blemish-size gauge.

DESCRIPTION OF THE PREFERRED EMBODIMENTS

Figure 1:
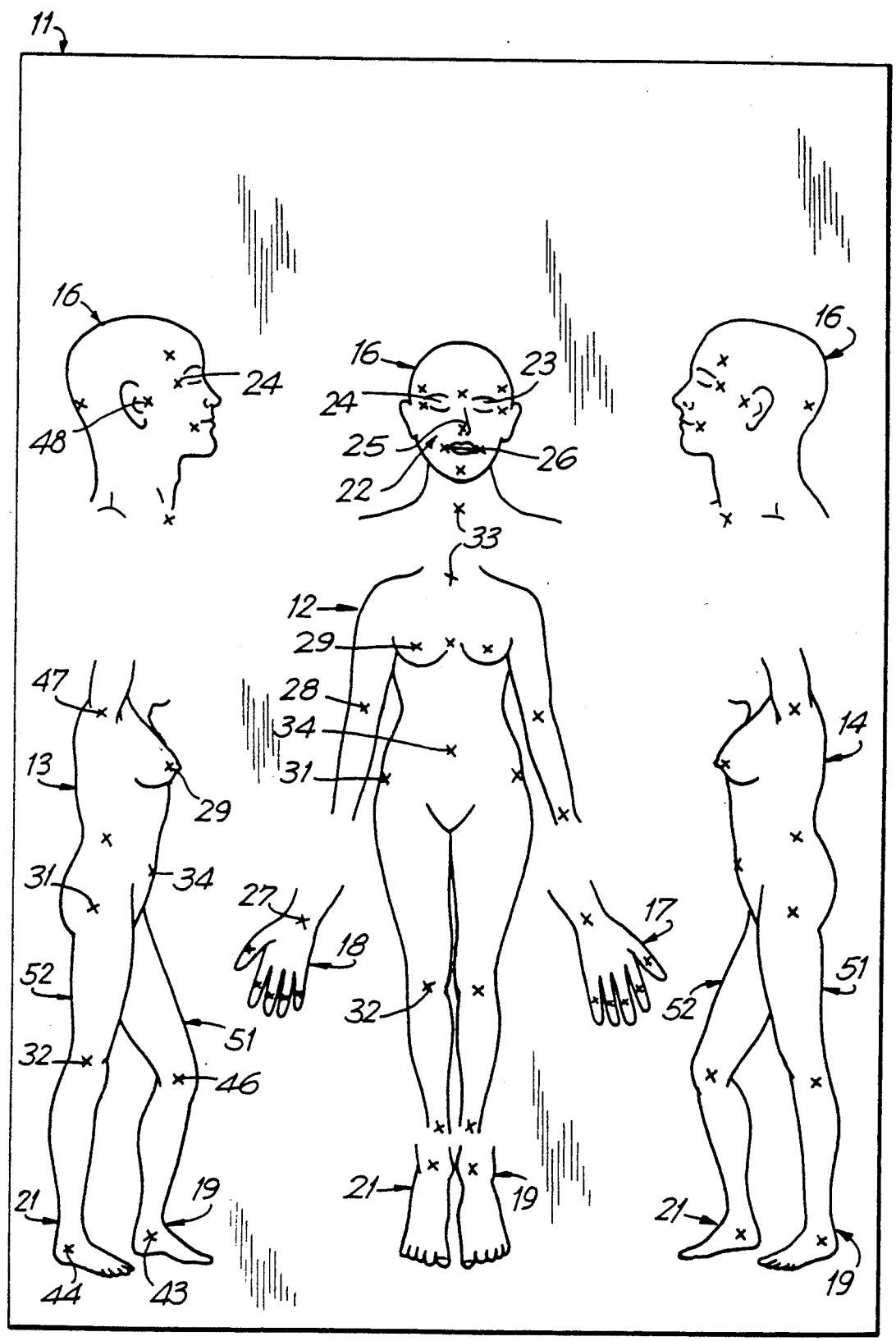
FIG. 1 is a plan view of a map of the front of the female human body, along with left and right side views and detailed close-ups of the head, hands and feet, including reference marks for recording the location of skin blemishes.

FIG. 1 illustrates a flat map 11 comprising a plurality of views of the female human body, including a frontal view 12, a right lateral view 13 and a left lateral view 14 suitable for use in the skin blemish measuring and recording system in accordance with the invention. Map 11 includes an outline of a frontal view of the female human body 12, including a head 16 at the top, a left hand 17 and right hand 18 at the respective sides and a top view of a left foot 19 and a right foot 21 at the bottom. A face 22 is depicted on head 16, including a left eye 23 and a right eye 24, a nose 25 and a mouth 26. Reference points marked with "X"s are provided at folds of skin and other easily discernable locations. These include points at a right wrist 27, a right elbow 28, a right breast 29, a right hip 31 and a right knee 32, with additional points on the corresponding (left) side of the body. Additional points are located between eyes 23 and 24 and at nose 25, sides of mouth 26, a neck 33, a navel 34 and other appropriate locations. A similar map depicting the male human body with its physical and anatomical differences, especially including the genitalia, is also contemplated.

Since certain areas of the body are more prone to skin blemishes due to increased exposure to the sun, it is desirable to provide magnified views of those areas. The greater area provided makes the detailed location and recording of each skin blemish easier and more convenient. Consequently, head 16, hands 17 and 18 and feet 19 and 21 are shown detached from the rest of front view 12 and enlarged in proportion to the rest of the body.

Looking at map 11, right lateral view of the female human body 13 is depicted on the left, and left lateral view of the female human body 14 is depicted on the right. These lateral views depict the same body as frontal view 12, similarly including enlarged head 16 shown detached at the top and feet 19 and 21 at the bottom. As in frontal view 12, right lateral view 13 and left lateral view 14 include reference points marked with "X"s at folds of skin and other easily discernable locations. For example, right lateral view 13 includes points at a left ankle 43 and a right ankle 44, a left knee 46 and right knee 32, right hip 31, navel 34, right breast 29, a right armpit 47, right eye 24, a right ear 48, a back of head 16 and other appropriate locations. Left lateral view 14 depicts reference points on the corresponding (left) side of the body, though similarly including points for both right and left ankles and knees. Moreover, in right lateral view 13 a left leg 51 is depicted extended away from the body so that it is not obscured by a right leg 52. Similarly, in left lateral view 14 a right leg 52 is showed extended away from the body so that it is not obscured by left leg 51. Arms are not depicted in lateral views 13 and 14 so that the body is not obscured.

Figure 2:
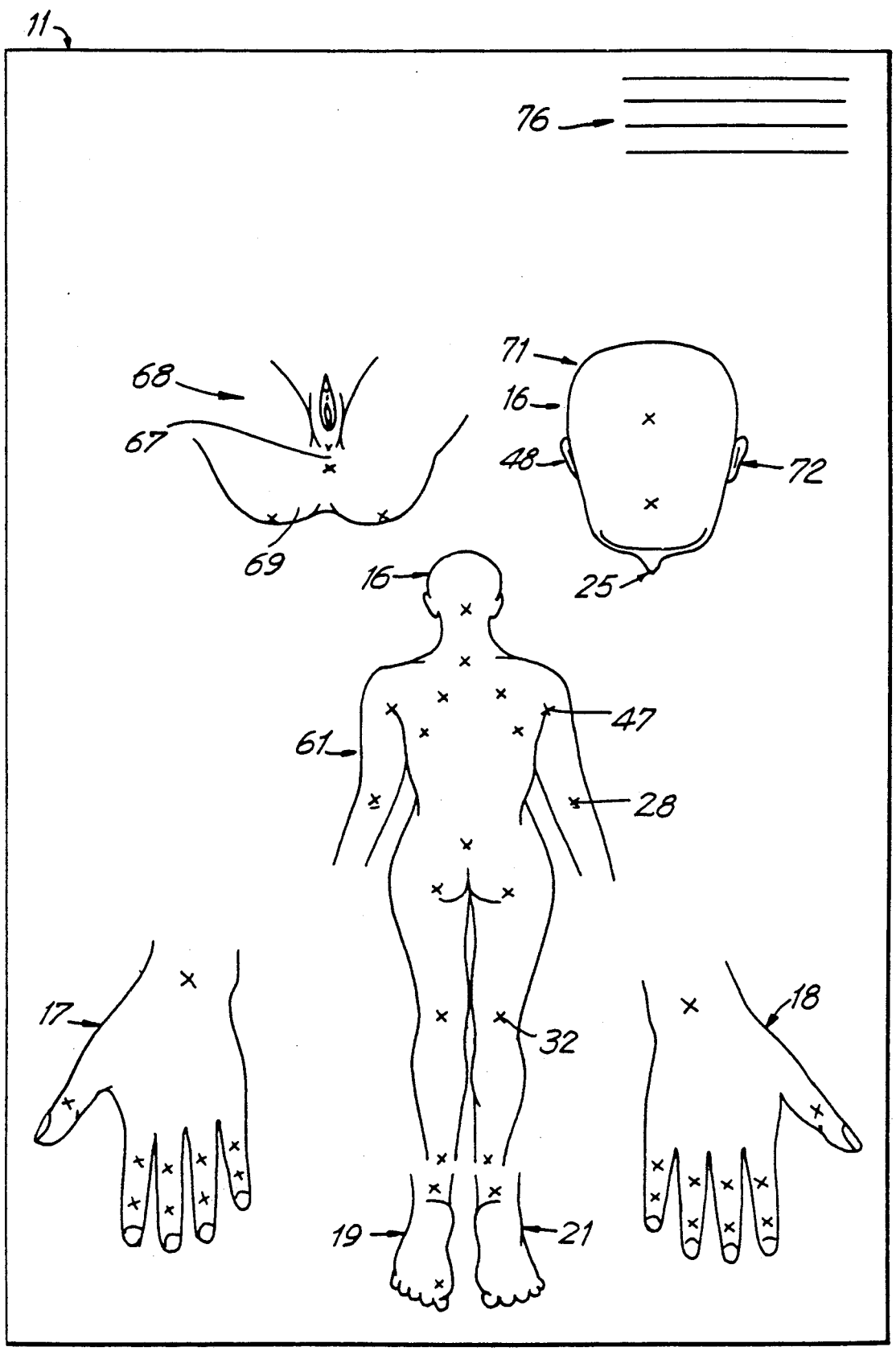
FIG. 2 is a plan view of a map of the rear of the female human body, along with detailed close-ups of the top of the head, the hands and feet and the perineal area, buttocks and upper thighs, for recording the location of skin blemishes.

FIG. 2 illustrates the opposite side of map 11 and shows a plurality of views, including similar outline of a rear view of the female human body 61 and other views and close-ups hereinafter discussed. Rear view 61 includes the back of head 16 at the top, an enlarged view of hands 17 and 18 at the respective sides with the backs showing and the bottom of enlarged feet 19 and 21 at the bottom. Hands 17 and 18 and feet 19 and 21 are shown detached from the body of rear view 61. As in FIG. 1, reference points marked with "X"s are provided at folds of skin and other easily discernable areas, including points at right elbow 28, right armpit 47 and the back of right knee 32, with additional points on the corresponding (left) side of the body. More points are located at the top and bottom of the back.

In addition to the enlarged views of hands 17 and 18 and feet 19 and 21, detailed close-ups of other parts of the female body are provided. These include a view 66 which depicts the perineal area 67, upper portions of the thighs 68 and portions of the buttocks 69 and a top view 71 of the head 16 (cephalic area). Top view 71 includes a left ear 72 and right ear 48 and nose 25 to indicate the front of the head. These detailed close-ups include reference points at appropriate locations similar to the other views of the body. Other close-ups, including the back and inside of the ears, the breasts and the top of the shoulders, are also contemplated, though this invention is not limited to illustrations of those areas and envisions detailed drawings of any part of the human body.

A space 76 is provided to record the subject's name, the doctor's name, the name of the person who performed the examination, and the date when the measurements were taken. This is shown at a corner on the back side of map 11, but could be provided on the front of map 11 or at any convenient location.

Figure 3:
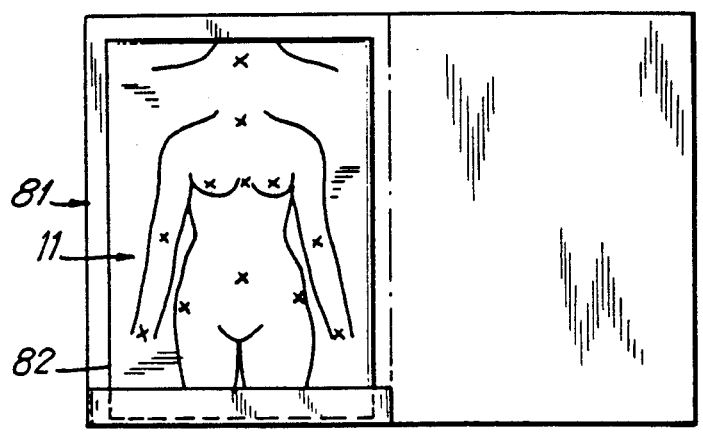
FIG. 3 is a plan view of the map of FIGS. 1 and 2 folded in an open folder for storage of the body map and for convenient recording of examination dates and other information.

In FIG. 3, map 11 is shown in a folded condition and stored within a storage folder 81. Map 11 is conveniently made larger than folder to facilitate recording of data and is designed to be folded up for easy storage. FIG. 3 shows map 11 folded along four fold lines into an area one-ninth the original size. Map 11 need not be fixed to folder 81 and can be made in any convenient size or be multiple sheets or pages with maps of various parts of the body.

Figure 4:
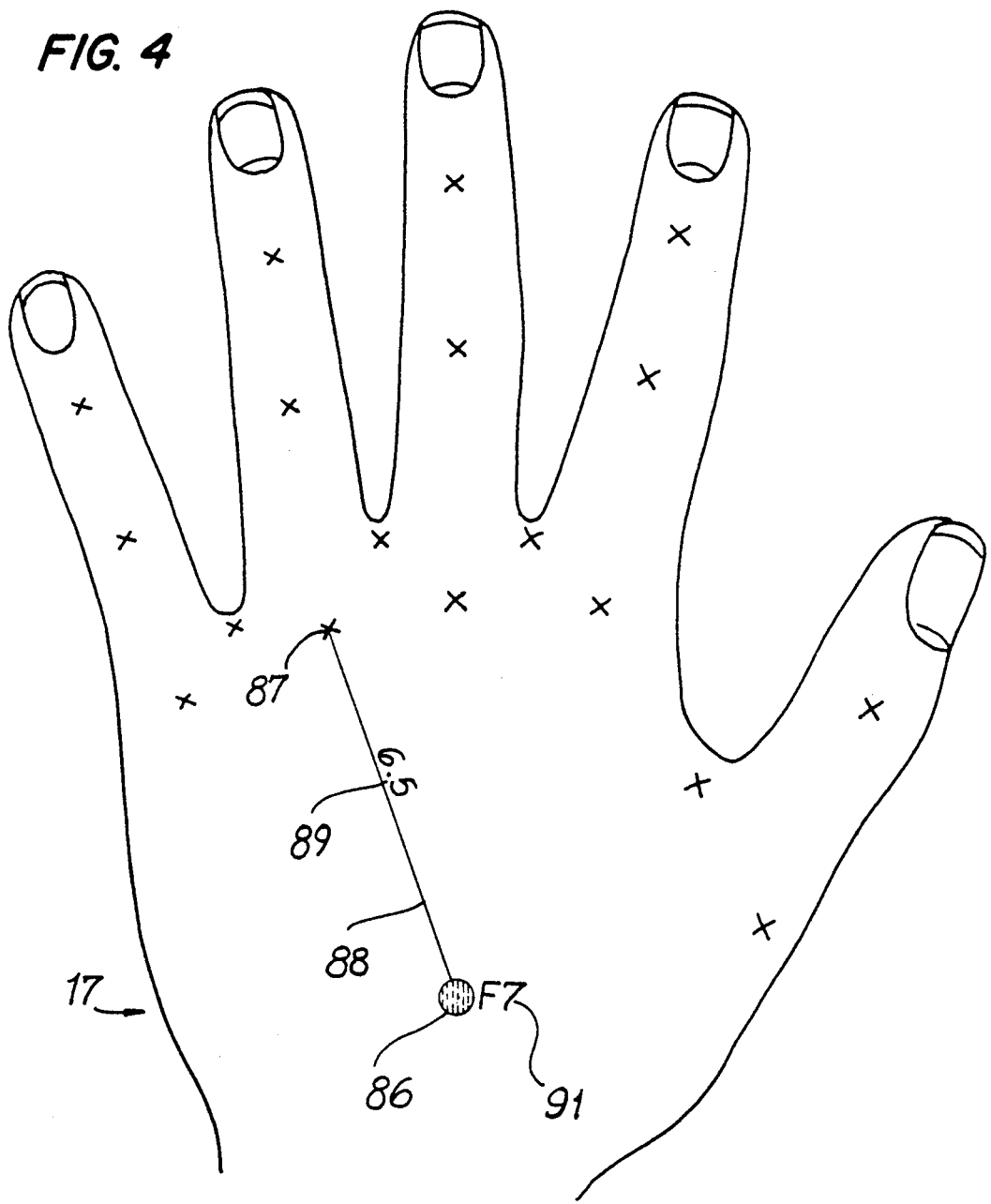
FIG. 4 is a detailed plan view of the back of a left hand showing reference points and a recorded blemish.

An illustration of the use of the map of the back of left hand 17 is shown in FIG. 4. Hand 17 includes several reference points marked with X's at the knuckles of the fingers and between each finger, along with other reference points at appropriate locations. A blemish 86 is shown at a measured distance from a reference point 87. Along a line 88 drawn from blemish 86 to reference point 87 is the distance 89 between the two points, with an individual letter and number designations 91 signifying the color and size of blemish 86 recorded near the blemish. This designation is determined utilizing a color scale 102, a blemish-size 103 and a distance scale 113 provided on a multifunctional device 101 shown in FIGS. 5 and 6 in accordance with this invention as will be described in more detail below.

The skin blemish measuring and recording system in accordance with the invention further includes a measuring device for determining the color of the blemish, measuring the size of the blemish and measuring the location on the body from one of the reference points on one of the maps of the body. As shown in FIG. 5, multi-functional measuring device 101 including three independent scales may be used. Measuring device 101 includes on a first side blemish-color scale 102 for determining the color of the blemish and blemish-size gauge 103 for determining the size of the blemish.

Color scale 102 is shown with 18 color regions in shades sufficient to portray a skin blemish, including shades of blues, blacks, browns, reds and other colors. It is contemplated that the color scale can include a lesser or greater number of colors, such as between 12 to 36, in order to depict a progression of typical observed colors of skin blemishes. Colors are adhered to measuring device 101 adjacent to a first edge 104 to facilitate direct comparison to a skin blemish. The colors of color scale 102 are further arranged in spectrum-like progressions, with individual letter designations 106 for each region located adjacent to each other. This is intended to be a standardized color and identification scale with individual designations 106 to regularize recording of colors and enable persons reviewing the findings to communicate results accurately. In a preferred embodiment, color scale 102 is made from ink or dye colors that are able to withstand exposure to heat, light and humidity without deterioration or change over an appropriate period of time. Further preferred embodiments contemplate color scale 102 disposed on a durable plastic material and if greater stability is desired, colors formed of azeotropic dyes.

Along an opposite edge 107 of measuring device 101 is size gauge 103 including a series of semi-circular cut-outs 108 or other shapes of increasing diameter (ranging from one millimeter to approximately twenty millimeters) cut out from measuring device 101. Each semi-circle 108 is located along edge 107 for easy sizing of the blemishes. Each semi-circle 108 has an individual number designation 109 for easy reference. In a preferred embodiment, corner 111 formed at edge 107 and a semicircle is rounded to avoid discomfort when placing size gauge 103 against a skin blemish for measurement.

Opposite side 112 of multi-functional measuring device 101 shown in FIG. 6 includes distance scale 113 along first edge 104. Size gauge 103 also appears on side 112 of measuring device 101 since it is cut out along opposite edge 107. Distance scale 113 is a metric scale from approximately 1 to 30 centimeters and is used to measure linear distance of a skin blemish from a reference point on one of the body maps. Distance scale 113 can also be used to measure blemishes which exceed the size of gauge 103. A multi-functional measuring device, in accordance with the invention, can also be provided with only two scales for use in the system, namely a color scale and a distance scale. In this case the distance scale can be used to measure the size of the blemish. However, the semicircular cut-outs 108 of size gauge 103 are more effective for accurately measuring size up to the size provided on the gauge.

In a preferred skin blemish measuring and recording kit prepared in accordance with the invention, folder 81 is used to store the components and to protect them from light, as shown in FIG. 3. Folder 81 can be conveniently used to store maps and the multi-functional measuring device. Most importantly, folder 81 may include an extended calendar/chart 82 for easy recording of the dates of the examinations and a history of the procedures and medications, along with sufficient space for the subject's name, the name of the doctor or other professional making the readings and other important data. Finally, folder 81 may be closed for easy storage and identification in a filing cabinet with other similar folders.

When the skin blemish measuring and recording system is used, the size and color of the blemish will be determined using blemish-size gauge 103 and color-reference scale 102. The distance from a reference point on map 11 will be determined using distance scale 113. A line can then be drawn on one of the maps from one of the selected reference point to the approximate location of the blemish. The distance from the reference point and the determined size and color from the gauges can be written along the drawn line. After the first complete examination, a suitable initial record for all visible skin blemishes will be part of the subject's permanent health history.

Figure 7:
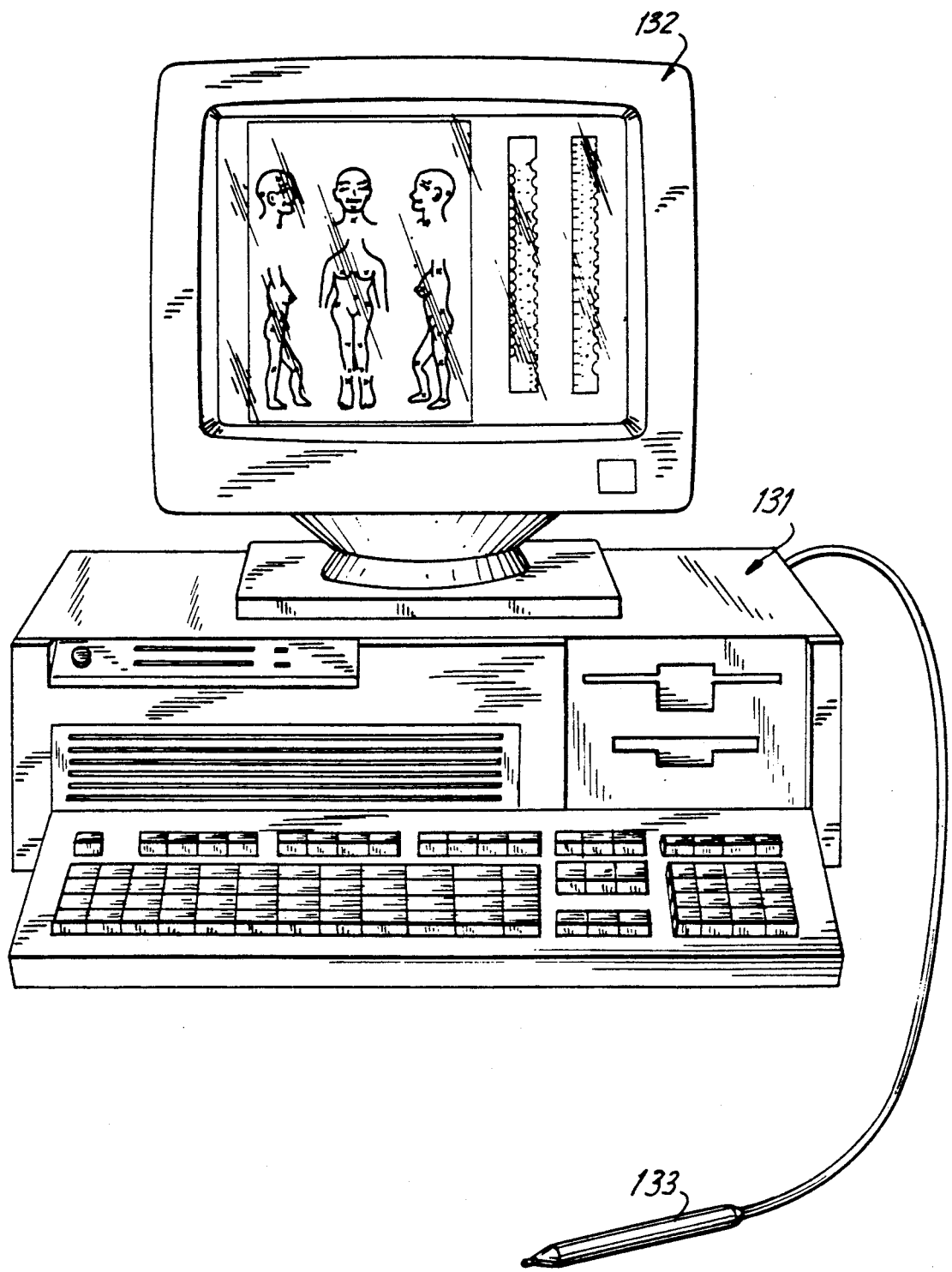
FIG. 7 is a view of an electronic recording device for use in practice of the invention.

The skin blemish measuring and recording system has been disclosed with respect to utilizing a flat map or chart of the human body for recording the findings. It is also contemplated that the system can record findings utilizing a computer 131 including a video monitor 132 and outfitted with a light pen input device 133, as shown in FIG. 7. The computer program would include the various maps or charts of the human body to be depicted on video screen 132. It is further contemplated that a voice recording device and/or audio-video device with or without voice-recording could be used to record the size, color and location of skin blemishes when used in conjunction with the color, size and distance measuring devices.

Multi-functional measuring device 101 would be utilized as in the earlier embodiments to classify the blemish as to size and color and utilize distance scale 113 to locate the blemish with respect to a body reference point. At the same time as showing the body map, display screen 132 can include the objective size scales which can be touched with light pen 133 to record the objective findings with respect to the particular blemish being recorded. Light pen 133 would then be used to touch video screen 132 at the appropriate location to record the findings.

The information input into computer 131 via light pen 133 and video screen 132 can then be easily generated in a print-out. The print-out can include the simple objective findings utilizing the objective scales of color size and location or can include a graphic representation of the body map showing the location of the letter and number indicating the color and size of the particular recorded blemish.

A significant feature of the skin blemish measuring and recording system in accordance with the invention is the establishment of a standardized blemish-color and blemish-size scale. By doing so this allows for a short-hand objective way to record and communicate findings. Use of a broad blemish-color scale formed of fade-resistant colors which will be shielded from light by the folder and an ultraviolet cover sheet disposed over the inks or dyes will permit the extended use of the multi-functional measuring device. This is significant because the changes in skin blemishes are subtle and may take many years to develop.

In order for the skin blemish measuring and recording system to be most meaningful, during the initial use all skin blemishes would be recorded to provide the user or health care professional with a starting point. This starting point would include the color, size and location of all found blemishes. Repeated observations and classification could take place during a regularly scheduled review such as once every two or three months, or once a year by either the subject who has the blemishes or by a health care professional.

The skin blemish measuring and recording system in accordance with the invention is easy to use and can record significant health-related information. The system is relatively easy to use since it includes only a direct color comparison with the colors provided along an edge of the measuring device to facilitate this and a convenient cut-out size gauge to facilitate size determination. It is contemplated that this could facilitate the early recognition of any changes in the size and/or color of blemishes, and the early recognition of new blemishes not previously recognized or recorded. The changes or recognition of new blemishes could facilitate the early diagnosis, by a professional health care provider, of disease, infection, cancer or any other ailment of the skin that displays characteristics of size or color, distinct from that of skin with a normal, healthy appearance. The system permits recording a quantitative record of skin blemishes with the ability to quantify any change in color or size from the original record.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all the generic and specific features of the invention herein described and all statements of the scope of the invention which, as a matter of language, might be said to fall between.

What is claimed is:

1. A skin blemish measuring and recording system, comprising:
   a body map depicting the human body with reference points for identifying locations on the body; and
   a measuring device including a blemish-color reference scale for determining color of a skin blemish and a distance measure for measuring blemish-size and location from skin folds and joints corresponding to reference points denoted on the body map.

2. The skin blemish measuring and recording system of claim 1, wherein the color-reference scale includes a plurality of color regions suitable for comparison to the actual color of a skin blemish.

3. The skin blemish measuring and recording system of claim 2, wherein the plurality of color regions of the color scale are denoted by standard reference indicia.

4. The skin blemish measuring and recording system of claim 2, wherein the plurality of color regions of the color scale are formed from in a manner to be appropriately free from deterioration and change in color.

5. The skin blemish measuring and recording system of claim 1, wherein the distance measure on the measuring device includes a blemish-size measuring gauge for determining the size of a skin blemish and a distance scale for measuring the distance of a skin blemish from a reference point on the body.

6. The skin blemish measuring and recording system of claim 5, wherein the measuring device is an elongated ruler and the color regions are disposed adjacent to one long edge of the ruler and the blemish-size measuring gauge is disposed on the opposed edge of that side of the ruler.

7. THe skin blemish measuring and recording system of claim 6, wherein the blemish-size measuring gauge is a series of cut-outs along the edge of the ruler, the cut-outs progressively increasing in size.

8. The skin blemish measuring and recording system of claim 7, wherein the blemish-size cut-out regions range in size from about 1 mm to 20 mm.

9. The skin blemish measuring and recording system of claim 7, wherein the distance scale is located on the opposite side of the ruler from the blemish-color scale.

10. The skin blemish measuring and recording system of claim 1, wherein the body map includes an outline of the front of a human body and an outline of the rear of the human body.

11. The skin blemish measuring and recording system of claim 10, wherein said map further includes view sufficient to show all surfaces of the skin.

12. The skin blemish measuring and recording system of claim 1, wherein the outline of the front of the human body is on one surface of a map sheet and the outline of the rear surface of the human body on another map sheet.

13. The skin blemish measuring and recording system of claim 1, wherein the outlines are on opposite sides of the same sheet.

14. A skin blemish measuring and recording kit, comprising:
   a body map depicting virtually all skin surfaces of the human body, including front and rear views, with reference points identifying distinguishable points of reference; and
   a measuring device including a blemish-color reference scale, a blemish-size measuring gauge and a distance scale.

15. A method for measuring and recording skin blemishes, comprising:
   determining the color of a skin blemish by comparison to a standard scale of skin blemish colors;
   determining the size of a skin blemish by comparison to a blemish-size gauge;
   determining the location of a skin blemish by measuring the distance from a body reference point; and
   recording the blemish color, blemish size and location from a reference point on a body map having reference points corresponding to skin folds and joints and other appropriate points of reference.

16. The method for measuring and recording skin blemishes of claim 15, wherein the blemish color, blemish size and location is recorded on a body map.

17. The method for measuring and recording skin blemishes of claim 15, wherein the blemish color and blemish size is determined by utilizing a measuring device including a blemish color scale and a distance scale.

18. A measuring device for determining the color and size of a skin blemish, comprising:
   an elongated ruler including a skin blemish color reference scale having a plurality of skin blemish colors in adjacent regions along one edge of the ruler and a skin blemish sizing scale including a plurality of progressively sized openings in the ruler.

19. The skin blemish measuring device of claim 18, further including a distance scale on the ruler.

20. The skin blemish measuring device of claim 18, wherein the skin blemish-size scale includes a plurality of progressively sized opening cut into the edge of the ruler opposite the color reference scale.

* * * * *